United States Patent

Bán et al.

Patent Number: 5,338,868
Date of Patent: Aug. 16, 1994

[54] PROCESS FOR PREPARING ALPHA-AMINO-PHENYLACETIC ACID-TRIFLUOROMETHANE SULFONIC ACID MIXED ANHYDRIDES

[75] Inventors: Károly Bán; Annamária Bán; Lajosné Páli; Márta Kruppa; Éva Somfai; Csaba Huszár, all of Budapest, Hungary

[73] Assignee: Chinoin Gyogyszer- es Vegyeszeti Termekek Gyara Rt., Budaest, Hungary

[21] Appl. No.: 689,828

[22] Filed: May 24, 1991

[30] Foreign Application Priority Data

Jul. 27, 1989 [HU] Hungary ............... 3818/89

[51] Int. Cl.$^5$ ............... C07D 305/12; C07C 229/00
[52] U.S. Cl. ..................... 549/323; 560/34; 560/35; 560/37
[58] Field of Search .................. 560/37, 34, 35; 549/323

[56] References Cited

U.S. PATENT DOCUMENTS 3,518,260  6/1970  Spencer et al. ............ 260/743
4,994,572  2/1991  Fleet ...................... 546/220

FOREIGN PATENT DOCUMENTS

0009609A3  4/1980  European Pat. Off.

OTHER PUBLICATIONS

Chem. Abstracts 95:209609m (1981).
Chem. Abstracts 94:66063v (1981).

*Primary Examiner*—C. Warren Ivy
*Assistant Examiner*—Raymond Covington
*Attorney, Agent, or Firm*—Herbert Dubno; Jonathan Myers

[57] ABSTRACT

A process is disclosed for the preparation of a compound of the Formula (VI)

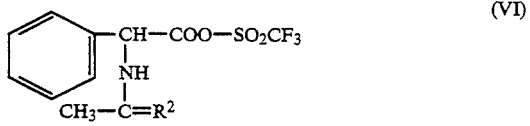

wherein
X is a hydrogen atom, or OH,
Y is a hydrogen atom, OH or a methyl group,
$R^2$ is a CH—COOR group, or a group of the formula (XI)

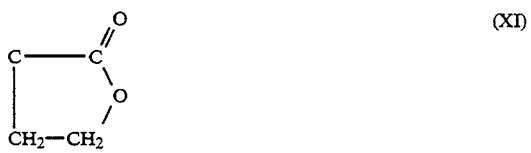

and
R is a $C_1$ to $C_2$ alkyl group, which comprises the step of: reacting a condensed salt of the Formula (IV)

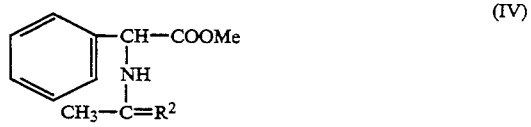

wherein Me is $Na^+$ or $K^+$, with a reactive derivative of trifluoromethane-sulfonic acid of the Formula (V)

$F_3C-SO_2OH.$

The compounds of the Formula (VI) are intermediates in the preparation of penicillins and cephalosporins with antibiotic activity.

4 Claims, No Drawings

PROCESS FOR PREPARING ALPHA-AMINO-PHENYLACETIC ACID-TRIFLUOROMETHANE SULFONIC ACID MIXED ANHYDRIDES

CROSS-REFERENCE TO RELATED APPLICATIONS

This application is a national phase of PCT/HU90/00051 filed Jul. 25, 1990 and based, in turn, on Hungarian National Application 3818/89 filed Jul. 27, 1989, under the International Convention.

The present invention relates to new valuable intermediates suitable for the acylation of 6-aminopenicillanic acids and 7-cephalosporanic acid in the production of pharmaceutical compositions. The present invention further provides a process for the preparation of said intermediate compounds and an improved process to prepare the known Dane salts.

The substituents in the formulae set forth herein are as follows:

X stands for hydrogen or OH,
Y stands for hydrogen, OH or methyl,
R stands for a $C_{1-2}$ alkyl group,
A stands for hydrogen, Me of $SO_2CF_3$, wherein Me stands for potassium or sodium ion
$R^1$ stands for $CH_2$—COOR or a group of the formula (IX)

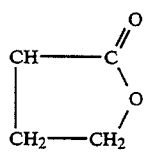

$R^2$ stands for CH—COOR or a group of formula (XI)

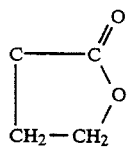

The present invention relates to a process for preparing a compound of the formula (I)

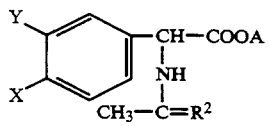

starting from an amino acid salt of the formula (II)

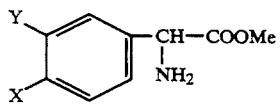

by forming a salt by reacting phenylglycine of the formula (VII)

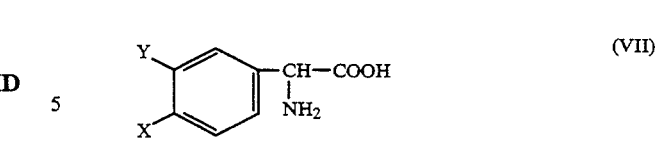

with 1.05–1.3 mole of alkalihydroxide in the presence of an alkanol and by reacting the reaction mixture with an acid having a pH value higher than 4.3 and by using 1.06–1.4 mole equivalent acid related to phenylglycine, the excess of alkali-hydroxide can be dissolved more selectively, while the amino acid salt of the formula (II) precipitates from the solution or by reacting the reaction mixture with an equivalent amount of alkali salts of the acids having a pH-value above 4.3 and by condensing the amino acid salt of the formula (II) obtained as described above or by any other method known per se in the presence of an alkanol with a ketone of the formula (VIII)

at the boiling point of the reaction mixture and removing continuously the formed water from the reaction mixture optionally by simultaneously adding a solvent by binary or ternary azeotropic distillation and upon cooling the reaction mixture, the condensed salt of the formula (IV)

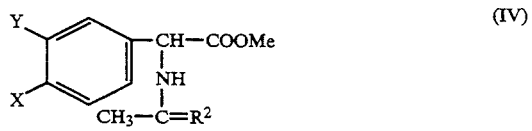

can be isolated from the reaction mixture in crystalline form.

According to our invention a salt of the formula (IV) can be reacted with a reactive derivative of the trifluoro-methane sulphonic acid of the formula (V)

preferably in the presence of a polar aprotic solvent.

The above processes can be used together or separately according to our present invention. The invention further extends to the novel compounds of the general formulae (IV), (VI)

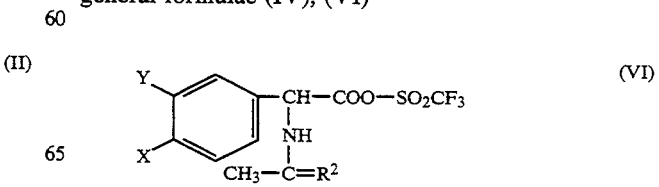

and (XIII).

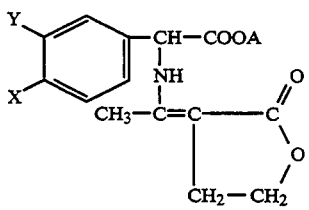

(XIII)

These compounds can be prepared from intermediates prepared by known methods. The present invention provides also analogous processes in the course of which the known intermediates leading to new compounds were prepared by any known method.

The present invention further relates to analogous processes for the preparation of the novel compounds as well.

BACKGROUND OF THE INVENTION

It is known that some beta-lactam acylated with D-2-phenylglycine are valuable pharmaceutically active compounds. Thus 6-amino-penicillanic acid acylated with D-2-phenylglycine is ampicillin and 7-amino-3-desacetoxy-cephalosporanic acid acylated with the above amino acid is also known as a semi-synthetic antibiotic called Cefalexin.

The above and similar synthetic antibiotics can be preferably prepared from D-2-phenylglycine by forming a potassium salt of N-(1-methyl-2-methoxy-carbonyl-vinyl)-D-2-phenylglycine or the potassium salt of N-(1-methyl-2-ethoxy-carbonyl-vinyl)-D-2-phenylglycine and preparing a mixed anhydride from the above compound and reacting same with a corresponding beta-lactam without isolation.

The enamine-salt prepared from D-2-phenylglycine was first prepared by Elizabeth Dane et al. [Chem. Ber. 98. 789-796 (1965)]. According to the process D-2-phenylglycine is boiled with the ethyl ester of acetoacetic acid and with potassium hydroxide and the product precipitating upon cooling is recrystallized from ethanol. Yield: 81.5%. The obtained product contains a half mole of crystal water which has to be removed before working up. According to Czechoslovakian patent application No. 147,194 the above reaction is carried out in ethanol. Yield: 75%.

The products obtained according to the above processes can be worked up according to Hungarian Patent 155,099 or German Patent 3,012,669.

It is also known that the acylated derivatives of 6-amino-penicillanic acid and 7-amino-cephalosporanic acid can be used in therapy as antibiotics of wide spectrum. One preferred representative of said compounds is D[(−)-α-amino-(para-hydroxy-phenyl)-acetamido)]-penicillanic acid (referred to hereinafter as amoxicillin).

The criteria which amoxicillin has to meet are disclosed at pages 3–4. Of the British Pharmacopoea 1973. One important criterium is the optical rotation of the product which is determined in the Pharmacopoea as: $(\alpha)_{20}{}^D = (+290°)-(+310°)$ (C=0.2% by weight/volume, water). Amoxicillin can be prepared from 6-amino-penicillanic acid or salt thereof and from a derivative of para-hydroxyphenylglycine according to British Patent 978,178. According to British Patent 1,339,605 6-amino-penicillanic acid is used in the form of its silylated derivative and the silyl group is removed after reaction. According to U.S. Pat. No. 3,674,776 the para-hydroxyphenylglycine derivative containing a protected amino-group is reacted with 6-amino-penicillanic acid or a salt thereof.

In the above patents the mixed anhydrides of β-keto-esters formed by condensation of alkyl esters of acetoacetic acid are mentioned as preferred out of the reactive derivatives formed on the amino group. The preparation of said compounds can be performed by a reaction of para-hydroxy-phenylglycine with an alkali hydroxide, by separation of the formed alkali salts by reacting with an alkyl ester of acetoacetic acid and conversion of the enamine to a mixed anhydride, preferably with chloroformic acid esters. The disadvantage of the process is that the purity of Amoxicillin prepared from a mixed anhydride obtained like this does not achieve the requirements of the Pharmacopoea. The optical rotation of Amoxicillin prepared according to the Examples of U.S. Pat. No. 3,674,776 is only $(\alpha)_D{}^{20} = +246.5°$ (c=0.1% in water). Purity of Amoxicillin in Example 1 of British Patent 1,339,605 is 80% by weight.

It is also known the Dane-salt was also prepared from para-hydroxyphenylglycine in methanol at the boiling point of the reaction mixture using an ester of acetoacetic acid and replacing the mixture by toluene at the end of the reaction and by crystallizing the product from toluene. This method using toluene can not be reproduced in industry because by increasing the size the mixture contains more and more unreacted alkali salt of amino acid and cannot be filtered.

In order to eliminate partially the above problems it has been suggested to add a lye to the system when preparing the Dane-salt (Hungarian Patent 182,519) or to use isopropanol as an alkanol (Hungarian Patent 186,143) by maintaining a narrow temperature range (65°-70° C.).

At a temperature higher than this a reesterification takes place. The above processes did not yield the desired improvement on industrial scale.

In each further step the mixed anhydride was formed with a chlorocarbonic acid ester forming an acylating agent.

The mixed anhydrides formed from the Dane-salt and chlorocarbonic ester can be well used for peptide chemical synthesis, but the preparation thereof is not without problems. Thus they can be prepared only at very low temperature (about −20° C.) and when using the very toxic chlorocarbonic esters under industrial conditions great care has to be paid and the costs are high.

SPECIFIC DESCRIPTION OF THE INVENTION

The novel triflates of the formula (VI) of the present invention are compounds which can be prepared relatively easily and are well determined and useful of the elimination for the above problems.

As a first step of the process of the present invention phenylglycine of the formula (VII) can be reacted preferably with potassium or sodium hydroxide in the presence of methanol or ethanol.

The reaction mixture is reacted preferably with acetic acid or propionic acid separating thereby the excess of alkali hydroxide.

According to our best knowledge we are the first to prepare the phenylglycine salt without residual lye and thereby both the salt and later the Dane-salts can be stabilized. The basis of this process is that we have recognized that by adding an acid with appropriate pK-value the contaminating lye excess can be selectively separated from the amine salt precipitating in crystalline form (the addition of which can not be avoided if the amine salt has to be prepared with a suitable yield).

In the course of the process of the invention about 10 percent more acid is used than would be necessary in order to bind the excess lye. This is due to the recognition that the presence of a catalytical amount of acid catalyzes the condensation reaction.

According to our invention we have first prepared such Dane-salt which was not prepared with an ester of acetoacetic acid but by using butyrolactone. This product can be similarly used like the classical Dane-salt prepared with the ester of aceto-acetic acid. The preparation and utilization is justified if the butyrolactone is more easily acessible or cheaper than the acetoacetate.

The $\beta$-keto-compound of the formula (VIII) is preferably used in an excess of about 30% by weight.

A further subject of the present invention is the removal of the water formed during the reaction when preparing Dane-salt by both methods.

We have recognized that Dane-salts crystallize with half a mole of water. This has been not mentioned in the literature. Therefore the later mixed anhydride formation can be performed with greater difficulty.

We have found that water obtained in the condensation reaction also appears in the form of crystal water. Several methods are given for removing water depending on the solvent used for the reaction sequence considering economical and other points of view.

We can proceed by performing the reaction in the presence of methanol and distilling off the methanol at the end of the reaction by adding to the reaction mixture a solvent which forms with water a binary mixture of minimal boiling point and removing the water by azeotropic distillation. It is preferred to add lower carboxylic acid esters or aromatic hydrocarbons, preferably diethyl carbonate, alkyl acetates, benzene, toluene, xylene or acetonitrile, and removing the water in the form of a binary mixture formed with said solvents.

If the reaction is performed in the presence of ethanol then the water formed during the reaction can be removed from the reaction mixture by azeotropic distillation. It can be more economical, if the ethanol is expensive to perform the condensation reaction in the presence of ethanol and adding at the end of the reaction a solvent which forms with water and ethanol a ternary mixture of minimal boiling point. Then the water is removed by ternary azeotropic distillation. As such solvents aromatic hydrocarbons or esters etc. can be mentioned.

In order to prepare the triflate one can preferably proceed by suspending the filter cake wet or dried Dane-salt in acetonitrile or nitromethane and reacting same at a temperature of 0° C. with trifluoromethane sulphonic acid-chloride added in small portions and without using any acid binding agent (see DE-PS 2,613,172 where the reaction is performed at $-20°-(-30)°$ C. in the presence of N-methyl-morpholine). The obtained mixed anhydride is well soluble in the applied solvent and can be separated by filtration from the alkali chloride formed in the reaction. The obtained solution can be directly used for further reaction and the active ingredient content amounts to 90% by weight according to HPLC analysis.

The acetonitrile solution can be diluted with ether or dichloromethane and the anhydride can be isolated in solid form.

In order to prepare enamines of homogeneous composition and in order to avoid reesterification it is desireable to use such alcohol which esterifies the acetoacetic acid.

SPECIFIC EXAMPLES

The invention is illustrated by the following, non-limiting examples.

EXAMPLE 1 a.) 167 g of D(—)-2-(p-hydroxyphenyl)-glycine are added to 57 g of potassium hydroxide dissolved in 1050 ml of methanol. The mixture is stirred until a clear solution is obtained. To the solution 150 g of acetoacetic acid methylester are added and the mixture is boiled for 90 minutes at 68° C. After about 40 minutes the precipitation of crystals is observed. Heating is continued and 2100 ml of acetonitrile are passed into the mixture within 20 minutes and changing to descending distillation the methanol is distilled off, while during the next 75 minutes, an additional 2100 ml of acetonitrile are added to the reaction mixture. Thereafter the suspension obtained is cooled to 20° C., after filtration the crystals are washed with acetonitrile and dried. 294 g of D(—)-(N-(2-methoxy-carbonyl-1-methyl-vinyl)-$\alpha$-amino-(p-hydroxy-phenyl)-acetic-acid potassium salt are obtained (yield 97%).

b.) From the salt obtained an amount of 30.3 g are suspended in 300 ml of acetonitrile and at 0° C., within 30 minutes 18 g of trifluoro-methane-sulphonic acid chloride are added dropwise. The mixture is stirred at room temperature for 1 hour in the course of which the suspension becomes a solution. Thereafter it is diluted with 500 ml of dichloro-methane (or ether) and the suspension thus obtained is kept at room temperature for 1 hour, thereafter it is filtered, washed with dichloro-methane and dried in vacuo. 35.5 g of D(—)-N-(2-methoxy-carbonyl-1-methyl-vinyl)-$\alpha$-amino-(p-hydroxy-phenyl)-acetic acid and trifloro-methane-sulphonic acid are obtained as a mixed anhydride.

Mp.: 78°–83° C. (decomposes).

| Analysis: | C% | H% | N% | F% |
| --- | --- | --- | --- | --- |
| calculated: | 42.38 | 3.53 | 3.53 | 14.35 |
| found: | 42.28 | 3.59 | 3.48 | 14.41 |

EXAMPLE 2

One proceeds according to Example 1a.), with the difference, that potassium hydroxide is replaced by 41 g of sodium hydroxide and methanol by 1050 ml of ethanol and aceto-acetic acid methylester is replaced by 170 g of acetoacetic acid ethylester.

270 g of sodium salt of D(—)-N-(2-ethoxycarbonyl-1-methyl-vinyl)-$\alpha$-amino-(p-hydroxyphenyl)-acetic acid are obtained.

EXAMPLE 3

150 g of trifluoro-methane-sulphonic acid and 56 g of phosphorous trichloride are stirred for 4 hours at 60° C. The reaction mixture is cooled to 0° C. without stirring. After 4 hours from the solidified polyphosphoric acid produced, the acid chloride is poured off and is used in the further reaction. Bp.: 113°–117° C. (1–2 bar).

EXAMPLE 4

In 1500 ml of methanol 60 g of sodium hydroxide are dissolved. After solution 239 g of D-p-hydroxy-phenylglycine are added and the mixture is stirred for 15 minutes at 60° C. Thereafter 195 g of α-acetyl-α-butyrolactone and 3 ml of acetic acid are added. The reaction mixture is boiled under reflux for 90 minutes and 1000 ml of methanol are distilled off. The remaining part is cooled to 20° C. and the suspension obtained is filtered. The remainder left on the filter is washed with cold acetonitrile, dried in vacuo. 270 g sodium salt of D(−)-N-(-1-methyl-2-(2'-oxo-tetrahydro-furan)-3-yl-vinyl)-α-amino-(p-hydroxy-phenyl)-acetic acid are obtained.

| Analysis: | C% | H% | O% | N% |
|---|---|---|---|---|
| Calculated: | 56.19 | 4.68 | 26.76 | 4.68 |
| found: | 56.27 | 4.78 | 26.71 | 4.61 |

Active ingredient content: 96.8% by titration with perchloric acid.

EXAMPLE 5

29.2 g of D(−)-N(1-methyl-2-(2'-oxo-tetrahydro-furan)-3-yl-vinyl)-α-amino-(p-hydroxy-phenyl)-acetic acid salt are suspended in 150 ml of acetonitrile and at 0° C. in the course of 30 minutes 17 g of trifluoromethane-sulphonic acid chloride are added dropwise. After stirring at 0°–5° C. for another half an hour the reaction mixture is allowed to warm to room temperature. The solution obtained contains D(−)-N(-1-methyl-2-(2'-oxo-tetrahydro-furan-3'-yl)-vinyl)-α-amino-(p-hydroxy-phenyl)-acetic acid-trifluoro-methane-sulphonic acid-anhydride. The transformation was 90% (HPLC). The solution can be used for further reactions.

EXAMPLE 6

25.2 g of potassium hydroxide are dissolved in 450 ml of methanol and 75 g of p-hydroxyphenylglycine are added. The mixture is stirred for 15 minutes at 60° C. and 4 ml of acetic acid and 75 g of acetoacetic acid ethylester are added. The suspension thus obtained is refluxed for 90 minutes, whereafter the methanol is distilled off, while ethylacetate is added dropwise until clear ethylacetate is distilled. The remainder is cooled to 20° C. and the suspension is filtered, the product obtained is washed with ethylacetate and dried in vacuo at 60° C. 129.2 g of potassium-D-N-(2-ethoxycarbonyl-1-methyl-vinyl)-α-amino-(p-hydroxy-phenyl)-acetate are obtained. Active ingredient content: 97.5%.

$[\alpha]_D^{20} = -87°$ (c=2, n HCl).

EXAMPLE 7

18.0 g of sodium hydroxide are dissolved in 450 ml of ethanol and 75 g of p-hydroxyphenylglycine are added. After stirring for 15 minutes at 60° C. 4 ml acetic acid and 72 g of acetoacetic acid methylester are added to the reaction mixture. After refluxing for 90 minutes 250 ml of ethanol are distilled off, the residue is cooled to 0° C. and the suspension is filtered, the crystals obtained are dried in vacuo at 60° C. 132.4 g of sodium-D-N-(2-methoxycarbonyl-1-methyl-vinyl)-α-amino-(p-hydroxy-phenyl)-acetate are obtained.

Active ingredient content: 98.4%.

$[\alpha]_D^{20} = -85°$ (c=2, n HCl).

EXAMPLE 8

18 g of sodium hydroxide are dissolved in 400 ml of ethanol and 75 g of p-hydroxyphenylglycine are added. After stirring for 15 minutes at 60° C., 10 ml of acetic acid and 75 g of acetoacetic acid ethylester are added to the reaction mixture. Refluxing for 90 minutes 100 ml of benzene are added and 200 ml of a water-benzene-ethanol ternary azeotrope are distilled off. The residue is cooled to 0° C. and the suspension is filtered, the crystals obtained are dried in vacuo at 60° C. 134.1 g of sodium-D-N-(2-ethoxycarbonyl-1-methyl-vinyl)-α-amino-(p-hydroxy-phenyl)-acetate are obtained.

Active ingredient content: 98.7%

$[\alpha]_D^{20} = -86°$ (c=2, n HCl).

EXAMPLE 9

18 g of sodium hydroxide are dissolved in 450 ml of methanol and 75 g of p-hydroxyphenylglycine are added and it is stirred for 15 minutes at 60° C. Thereafter 2 ml of acetic acid and 75 g of acetoacetic acid ethylester are poured into the reaction mixture and after refluxing for 90 minutes the methanol distillation starts. At the same time toluene is added at the rate of the distillation and the addition is continued until the vapor temperature reaches 100° C. Thereafter the suspension obtained is cooled to 20° C., filtered and the crystals obtained are washed with a double amount of toluene. They are dried at 60° C. in vacuo. 135.2 g of sodium-D-N-(2-ethoxycarbonyl-1-methyl-vinyl)-α-(amino-(p-hydroxy-phenyl)-acetate are obtained. Boiling the product in methanol 120.7 g of a pure salt are obtained.

Active ingredient content: 99.5%

$[\alpha]_D^{20} = -87.5°$ (c=2, n HCl).

Sulphate ash: 23.5%

The quality does not change during storage for 30 days (room temperature, air).

EXAMPLE 10

The process is identical with that of example 9.) with the difference, that instead of toluene, xylene is used and the distillation is continued until a vapor temperature of 120° C. is reached.

134.7 g of sodium-D-N-(2-ethoxy-carbonyl-1-methyl-vinyl)-α-amino-(p-hydroxy-phenyl)-acetate are obtained. Active ingredient content. 98.7%.

$[\alpha]_D^{20} = -86°$ (c=2, n HCl).

EXAMPLE 11

The process is identical with that of example 9 with the difference, that instead of toluene, butyl-acetate is used. 134.9 g of sodium-D-N-(2-ethoxycarbonyl-1-methyl-vinyl)-α-amino-(p-hydroxy-phenyl)-acetate are obtained.

Active ingredient content: 98.9%.

$[\alpha]_D^{20} = -86.5°$.

EXAMPLE 12

The process is identical with that of example 8 with the difference, that instead of benzene butyl-acetate is applied. A water-ethanol-butyl-acetate ternary mixture is distilled off.

133.7 g of sodium-D-N-(2-ethoxycarbonyl-1-methyl-vinyl)-α-amino-(p-hydroxy-phenyl)-acetate are obtained.

Active ingredient content: 98.4%.

$[\alpha]_D^{20} = -86.5°$ (c=2, n HCl).

EXAMPLE 13

18 g of sodium hydroxide are dissolved in 250 ml of methanol and 75 g of p-hydroxy-phenyl-glycine are added. After stirring at 60° C. for 15 minutes 2 ml of acetic acid is added to the reaction mixture which is cooled to 0° C. and the suspension is filtered. The wet p-hydroxy-phenyl-glycine sodium salt obtained is suspended in 500 ml of ethanol, 75 g of acetoacetic acid methylester and 0.5 ml of acetic acid are added and the mixture is refluxed for 90 minutes. The residue is cooled to −5° C. and the suspension obtained is filtered, the crystals are dried in vacuo at 60° C. 124.1 g of sodium-D-N-(2-methoxy-carbonyl-1-methyl-vinyl)-α-amino-(p-hydroxy-phenyl)-acetate are obtained.

Active ingredient content: 99.4%.
$[\alpha]_D^{20} = -86°$ (c=2, n HCl).
Sulphate ash: 23.6%.

EXAMPLE 14

40 g of sodium acetate and 75 g of p-hydroxyphenylglycine are refluxed in 500 ml of ethanol for 2 hours. To the suspension obtained 0.5 ml of propionic acid and 75 g of acetoacetic acid ethylester are added and the mixture is refluxed for additional 90 minutes under distillation. A fraction of 330 ml is distilled off. The suspension obtained is cooled to −5° C., then filtered and the crystals are washed with ethylacetate and dried in vacuo at 60° C. 126.1 g of sodium-D-N-(2-ethoxycarbonyl-1-methyl-vinyl)-α-amino-(p-hydroxy-phenyl)-acetate are obtained.

Active ingredient content: 99.1%.
$[\alpha]_D^{20} = -86°$.
Sulphate ash: 23.7%.

By evaporation of the mother liquor an additional 7-9 g of product as a second batch are obtained.

EXAMPLE 15

18 g of sodium hydroxide are dissolved in 600 ml of methanol and 67 g of D(−)-phenylglycine are added. After stirring for 15 minutes at 60° C. a clear solution is obtained. To this solution 2 ml of acetic acid and 75 g of acetoacetic acid-ethylester are added. The solution is refluxed for 90 minutes whereafter a fraction of 350 ml is distilled off. The suspension obtained is cooled to −5° C., filtered and the crystals are dried in vacuo at 60° C. 126.8 g of sodium-D-N-(2-ethoxycarbonyl-1-methyl-vinyl)-α-amino-phenyl-acetate are obtained. Active ingredient content: 98.2%.

$[\alpha]_D^{20} = -84.5°$ (c=2, n HCl).

Quality remains unchanged after a storage of 30 days (stored at room temperature).

EXAMPLE 16

40 g of sodium acetate and 67 g of D(−)-phenyl-glycine are added to 600 ml of ethanol. The mixture is refluxed for 2 hours and 75 g of acetoacetic acid-ethylester are added and the mixture is refluxed for 90 minutes. A fraction of 330 ml is distilled off and the residue is cooled to −5° C., filtered and the crystals obtained are dried at 60° C. in vacuo. 124.5 g of sodium-D-N-(2-ethoxy-carbonyl-1-methyl-vinyl)-α-amino-phenyl-acetate are obtained. Active ingredient content: 98.2%.

$[\alpha]_D^{20} = -84.5°$ (c=2, n HCl).

EXAMPLE 17

18 g of sodium hydroxide are dissolved in 600 ml of ethanol and 81 g of 3-methyl-4-hydroxy-phenyl-glycine are added. After stirring for 15 minutes at 60° C. 2 ml of acetic acid and 75 g of aceto-acetic acid-ethylester are added. After boiling for 90 minutes a fraction of 350 ml is distilled off. The remainder is cooled to −5° C., The suspension is filtered and the crystals obtained are dried in vacuo at 60° C. 136.1 g of sodium-D-N-(2-ethoxycarbonyl-1-methyl-vinyl)-α-amino-(3-methyl-4-hydroxyphenyl)-acetate are obtained.

Active ingredient content: 96.4%.
$[\alpha]_D^{20} = -82°$ (c=2, n HCl).

What we claim is:

1. A process for the preparation of a compound of the Formula (VI)

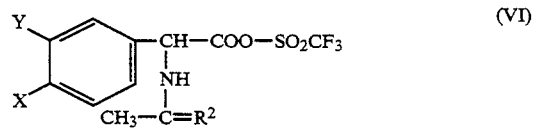

wherein
X is a hydrogen atom or OH;
Y is a hydrogen atom, OH or a methyl group;
$R^2$ is a CH—COOR group, where R is a $C_{1\ to\ 2}$ alkyl group, or $R^2$ is a group of the Formula (XI)

wherein a condensed salt of the Formula (IV)

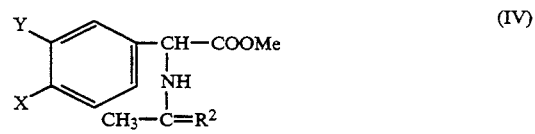

wherein Me is a sodium or potassium cation, is reacted with a reactive derivative of trifluoromethane-sulfonic acid of the Formula (V)

2. Process according to claim 1, wherein the condensed salt is reacted with the trifluoromethane-sulphonic acid-chloride at a temperature of 0°-5° C.

3. The process defined in claim 1 wherein the compound of the Formula (VI) is selected from the group consisting of:
D(−)-N-(2-methoxycarbonyl-1-methyl-vinyl)-alpha-amino-(p-hydroxy-phenyl)-acetic acid-trifluoromethane sulfonic acid anhydride; and
D(−)-N-(1-methyl-2-(2'-oxo-tetrahydro-furan-3'-yl)-vinyl)-alpha-amino-(p-hydroxyphenyl)-acetic acid-trifluoromethane sulfonic acid anhydride.

4. The process defined in claim 1 wherein the compound of the Formula (VI) is D(−)-N-(1-methyl-2-(2'-oxo-tetrahydro-furan-3'-yl)-vinyl)-alpha-amino-(p-hydroxyphenyl)-acetic acid-trifluoromethane sulfonic acid anhydride.

* * * * *